US00PP35170P2

(12) United States Plant Patent
Hansen

(10) Patent No.: US PP35,170 P2
(45) Date of Patent: May 16, 2023

(54) ***HIBISCUS* PLANT NAMED 'VALENTINE'S CRUSH'**

(50) Latin Name: ***Hibiscus* hybrid (L.)**
Varietal Denomination: Valentine's Crush

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 17/803,783

(22) Filed: Nov. 22, 2022

(51) Int. Cl.
*A01H 5/00* (2018.01)
*A01H 6/60* (2018.01)

(52) U.S. Cl.
USPC ..... Plt./257

(58) Field of Classification Search
USPC ..... Plt./257
See application file for complete search history.

*Primary Examiner* — Susan McCormick Ewoldt

(57) ABSTRACT

A new and distinct cultivar of winter-hardy, herbaceous, perennial, hybrid *Hibiscus* plant named 'Valentine's Crush' comprising an upright mounded habit of multiple, well-branched, basal stems producing flowers from the bottom to the top of the plant from late July to early September. Flowers have highly-overlapping petals of bright-red with a slightly-shiny dark red shiny eye. The foliage is variably cleft to incised tri-lobed, and dark-green colored.

2 Drawing Sheets

Botanical classification: *Hibiscus* hybrid (L.).
Variety denomination: 'Valentine's Crush'.

STATEMENT REGARDING PRIOR DISCLOSURES UNDER 37 CFR 1.77(b)(6)

The first publically released information of the new plant was on Dec. 1, 2021 when it was displayed with a photograph and brief non-enabling description on websites operated by Walters Gardens, Inc. and Proven Winners®, followed on Jun. 8, 2022, as a photograph and brief description in the "Walters Gardens 2022-2023 Catalog. followed with a non-enabling description and photograph in the "Walters Gardens, Inc. 2022-2023 Catalog on Jun. 8, 2022. Walters Gardens, Inc and Proven Winners® obtained the new plant and all information about the new plant from the inventor. The first disclosure, in the form of a sale, was made by Walters Gardens, Inc. on Apr. 11, 2022. Walters Gardens, Inc. obtained the new plant and all information relating thereto, from the inventor. No plants of *Hibiscus* 'Valentine's Crush' have been sold, in this country or anywhere in the world, by any name, nor has any disclosure of the new plant been made more than one year prior the filing date of this application, and such sale or disclosure within one year was either derived directly or indirectly from the inventor.

BACKGROUND AND ORIGIN OF THE PLANT

The present invention relates to the new and distinct hardy, herbaceous, *Hibiscus* plant, *Hibiscus* 'Valentine's Crush' hybridized under the direction of the inventor on Jul. 31, 2018, at a wholesale perennial nursery in Zeeland, Mich. The new plant is a hybrid of the unreleased, proprietary hybrid known as 16-134-1 (not patented) times the unreleased, proprietary hybrid known as 16-154-3 (not patented). Into the trial process the new plant was assigned the breeder code labeled 18-126-4. Both parents have a complex mixture of species in them, comprising the species: *moscheutos* and *coccineus*.

*Hibiscus* 'Valentine's Crush' was first asexually propagated in the late summer of 2020 by sterile shoot-tip tissue culture and later by shoot-tip cuttings at the same nursery in Zeeland, Mich. The resultant asexually propagated plants have found both propagation methods to be stable and true to type in successive generations of asexual reproduction.

BRIEF SUMMARY OF THE PLANT

*Hibiscus* 'Valentine's Crush' differs from its parents as well as all other hardy herbaceous *Hibiscus* known to the applicant in many traits. The most similar *Hibiscus* known to the applicant are: 'Cranberry Crush' U.S. Plant Pat. No. 21,984, 'Holy Grail' U.S. Plant Pat. No. 31,478, 'Candy Crush' U.S. Plant Pat. No. 32,587, 'Mars Madness' U.S. Plant Pat. No. 27,838, 'Midnight Marvel' U.S. Plant Pat. No. 24,079, and 'Vintage Wine' U.S. Plant Pat. No. 27,839.

'Cranberry Crush' has a smaller and broader habit with flowers that are more cupped and petals of a more scarlet reddish color. 'Holy Grail' has a slightly shorter and broader habit, deeper burgundy tinted foliage, with flowers that are darker red with a much deeper red eye. 'Candy Crush' has a slightly shorter and broader habit with white flowers having deep pink distal blushing and veins and a dark-red eye. 'Mars Madness' has a slightly shorter and much broader habit and flowers that are more magenta-red. 'Midnight Marvel' has a more rounded habit with larger flowers of scarlet-red. 'Vintage Wine' has ovate leaves with less burgundy coloration, and the flowers are smaller with deeper scarlet-red petals.

The female parent comparison is not possible as neither notes, photographs nor plants were maintained. The male parent comparison is not possible as neither notes, photographs nor plants were maintained.

*Hibiscus* 'Valentine's Crush' is a unique hardy herbaceous *Hibiscus* with the following combined traits:

1. Winter-hardy compact perennial with an upright mounded habit of multiple, well-branched, basal stems;
2. Many rotate flowers of bright-red with a slightly-shiny dark-red eye produced from the bottom to top of the plant;
3. Petals are highly overlapping and open flat giving good show from nearly any angle;
4. Flowers produced over a long period from late July to early September;
5. Variably cleft to incised tri-lobed foliage of dark green color.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source, and direction may cause the appearance of minor variation in color.

DETAILED BOTANICAL DESCRIPTION

Figure 1:
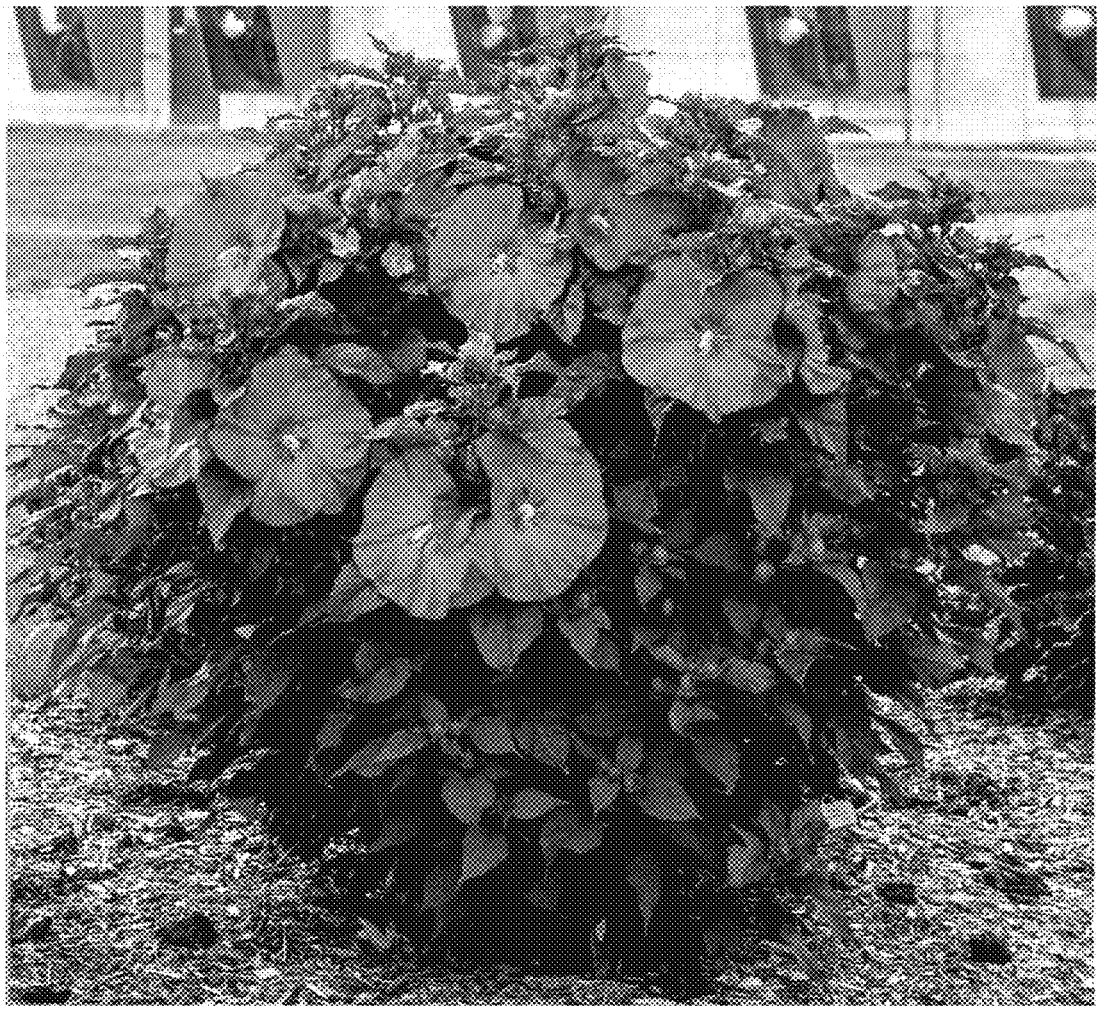
FIG. 1 shows a three-year-old plant in full flower in a display garden.
Figure 2:
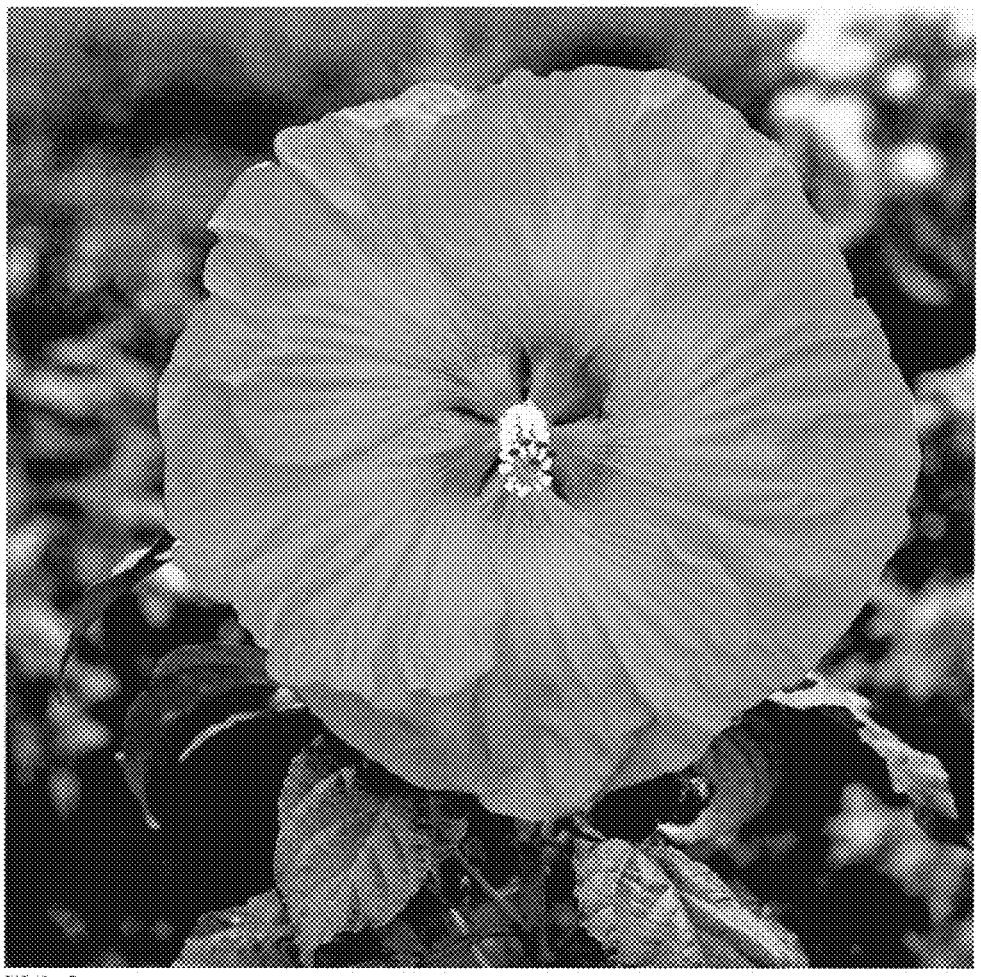
FIG. 2 shows a close-up of the flower and bud.

The following descriptions and color references are based on the 2015 edition of The Royal Horticultural Society Colour Chart except where common dictionary terms are used. The new plant, *Hibiscus* 'Valentine's Crush', has not been observed in all possible environments. The phenotype may vary slightly with different environmental conditions, such as temperature, light, fertility, moisture, and maturity levels, but without any change in the genotype. The following observations and size descriptions are of three-year-old plants in a loamy-sand, full-sun display garden of a nursery in Zeeland, Mich., with supplemental fertilizer and water as needed. The plants are of natural habit and were not treated with plant growth regulators, nor were they pinched at any time in the growth year.

Parentage: The female or seed parent is the unreleased, non-patented, proprietary *Hibiscus* known by the breeder code 16-134-1, the male or pollen parent is the unreleased, non-patented, proprietary *Hibiscus* known by the breeder code 16-154-3;

Propagation:

*Method.*—Shoot tip cuttings and sterile shoot-tip plant tissue culture division.

*Time to initiate roots from tissue culture.*—About two weeks.

*Rooting habit.*—Normal, branching, developing thick to about 2.2 cm diameter, fleshy; root color creamy yellow nearest RHS 161D depending on soil type.

*Crop time.*—Under normal summer growing conditions 12 to 16 weeks to flower in a four-liter container from cutting. Plant vigor is very good.

Plant description:

*Plant habit.*—Hardy herbaceous perennial with about 16 thick, upright, heavily-branched stems producing an upright spreading mound to about 145 cm tall and about 155 cm wide; flowering in distal one-third of plant with up to about 40 flowers per main stem, average flowers per stem about 32.

*Stem.*—Cylindrical, glabrous, glaucous; to about 144 cm tall and to about 44 mm diameter at base, average about 117 cm tall and about 25 mm diameter at base.

*Stem color.*—Proximally nearest RHS 145A with a light blush of RHS 183C, distally a blend of between RHS 145A and RHS 146D.

*Lateral branches.*—To 9 per stem, average about 7 per stem; cylindrical, glabrous, glaucous; to about 56 cm long and 9 mm diameter at base, smaller distally.

*Lateral branch color.*—Nearest RHS 145A.

*Internode.*—About 12 nodes per stem below branches and 21 below single flowers; average 40 nodes per stem; internode length about 3.0 cm of unpinched plant.

*Internode color.*—Same as surrounding stem.

Foliage description: Variably cleft to incised tri-lobed; alternate; coarsely and irregularly dentate; apex and side lobes acute; base rounded to cordate; glabrous abaxial and adaxial; dissected from 20% to 80% of the way to midrib; adaxial surface semi-lustrous when expanding, matte when mature; abaxial surface matte; leaf blades to about 21.5 cm long and about 23 cm across, average blade size 15 cm long and 13 cm wide; no fragrance detected;

*Foliage color.*—Young expanding leaves — adaxial nearest RHS NN137B, abaxial between RHS 147B and RHS 147C; mature leaves — adaxial nearest RHS NN137A, abaxial between RHS 147B and RHS 146B.

*Veins.*—Palmate; matte; costate on abaxial.

*Vein color.*—Adaxial midrib nearest RHS 181C in basal 35 mm, nearest RHS 147C distally, abaxial variably nearest RHS 182A, nearest RHS 187A, between RHS 182D and RHS 195B, and nearest RHS 146D.

*Petioles.*—Mostly cylindrical, proximally slightly applanate on adaxial side near base; glaucous; glabrous; to about 9 cm long and 6 mm across at base, average size about 7 cm long and 4.5 mm wide at base.

*Petiole color.*—Adaxial between RHS 146C and RHS 183C; abaxial nearest RHS 146D in basal 3 cm, lightly maculate to blushed with nearest RHS 183C distally in regions of high light.

Flower description: Complete; perfect; single; solitary; rotate; actinomorphic; mostly outward facing; lasting up to two days on plant; no fragrance detected;

Flower size: To about 22 cm across and 7 cm deep, decreasing distally; dark red shiny eye medium width, about 6 cm across;

Inflorescence: To 40 flowers per the main stem without pinching; flowering in distal 50 cm;

*Buds one day prior to anthesis.*—Ellipsoidal with rounded apex and bluntly truncate base; sepals adpressed to petals; to about 6 cm long and about 3.5 cm diameter in middle.

*Bud color one day prior to anthesis.*—Exposed petal color variable, nearest RHS 187B; calyx color nearest RHS 146B with strong distal blushing to nearly solid RHS 187A.

*Epicalyx.*—Typically, 11 per flower; linear; entire; glabrous and matte adaxial and abaxial; with margin ciliolate; sharply acute apex and truncate base, arcuate upwards around calyx near apex; about 33 mm long and about 3.5 mm wide at base.

*Epicalyx color.*—Adaxial distally nearest RHS 137B with strong blush near veins of nearest RHS 187A, abaxial distally nearest RHS 146A, adaxial and abaxial proximally nearest RHS 146B.

*Calyx.*—Campanulate, form star-shaped hypanthium; to about 27 mm deep and 50 mm wide at apices.

*Sepals.*—Five; ovate; narrowly acute apex; glabrous; margin entire, edentate; abaxial and adaxial surfaces matte; about 37 mm long, about 17 mm wide at fusion, fused in basal 14 mm.

*Sepal color.*—Adaxial between RHS 146C and RHS 147C with faint distal blushing of nearest RHS 187A, abaxial between RHS 146C and RHS 146B with strong distal blushing to nearly solid RHS 187A, and distal veins to nearest RHS 187A.

*Flower attitude.*—Mostly outwardly facing.

*Flower lastingness.*—Persist for one to two days; effective for four about 8 weeks beginning late July.

*Flower fragrance.*—No detectable fragrance.

*Petals.*—Five; glabrous adaxial and abaxial; adaxial eye zone lustrous and abaxial eye zone slightly lustrous, remaining distal adaxial portion and abaxial matte; adnate to the androecium to form a column, imbricate to about 40% overlapping at widest part (petals overlapping 40% to the petals on either side); undulation moderate; palmately veined, primary veins flat on adaxial and slightly costate abaxial; adaxial surface slightly pleated or folded in distal portion; apex rounded with distinct basal claw and limb; margins entire, edentate; without leading petal edge folded under itself.

*Petal size.*—Average about 14.5 cm across and about 11 cm long, claw base about 9 mm across (smaller in later part of flowering season).

*Petal color.*—Adaxial basal eye zone between RHS N187B and RHS N187C, distally between RHS 53B and RHS 53A with veins nearest RHS 53A; abaxial basal 2 mm nearest RHS NN155D, distally between RHS 53B and RHS 53A although closer to RHS 53B proximally and closer to RHS 53A distally.

*Flower lastingness.*—One to two days.

*Gynoecium.*—Single; partially enclosed in column. Column: glabrous and lustrous; about 4.5 cm long and about 12 mm across at base; with pistil exserted about 16 mm. Column color: variable, nearest RHS 53C. Style: puberulent in region exserted above column; about 5.5 cm long, pentafurcate in about distal 10 mm, branch diameter about 1 mm; color nearest RHS 53B in exposed portion and RHS NN155D enclosed in column. Stigma: five; flattened globose, puberulent, about 4 mm in diameter and 1 mm tall; color in center nearest RHS 53B, outer portion nearest RI-IS 59A. Ovary: superior; conical; longitudinally grooved; apex and flat truncate base; about 9 mm across at base and about 10 mm tall; acute apex; color nearest RHS 5D.

*Androecium.*—Numerous, about 100. Filaments: attached starting about 7 mm from base and to about 2 mm from the apex of column; to about 4 mm long and about 0.2 mm diameter; color nearest RHS 53B proximally and nearest RHS 56D distally. Anthers: flattened reniform; dorsifixed; about 2 mm long and 1 mm across and about 0.8 mm thick; color nearest RHS 12C. Pollen: abundant, globose, less than 0.1mm long; color nearest RHS 10A.

Pedicel: Cylindrical, glabrous in proximal portion and micro-puberulent in distal portion; matte; length from base of sepal to abscission point about 1 cm long, from abscission point to stem node about 9.5 cm long; about 4 mm diameter; longer on early flowers and decreasing in distal flowers; color nearest RHS 146C distal abscission point and RHS 146C with moderate blush of nearest RHS 181B proximal abscission point;

Peduncle: Cylindrical, glabrous, glaucous; to about 176 cm tall and about 45 mm diameter at base, average about 165 cm tall and about 25 mm diameter at base; flowering in upper 50 cm in center stems and nearly from the ground to apex in outer stems;

Peduncle color: Proximally nearest RHS 138A with light blush of RHS 181B, distally blend of nearest RHS 146C and RHS 181B to nearly solid RHS 181B;

Fruit: Penta-loculicidal capsule; pubescent along inner septa, glabrous outside; globose, acute apex and flattened base; about 27 mm long and 27 mm diameter; color nearest RHS 200A when mature; about 85 seeds per fruit;

Seed: Minutely hispidulous; globose; about 3.5 mm in diameter; color between RHS 200C and RHS 200D;

Resistance: *Hibiscus* 'Valentine's Crush' has not displayed any pest and disease resistance beyond that typical of hardy perennial *Hibiscus*. The plant grows best with plenty of moisture.

Hardiness at least from USDA zone 4 through 9.

I claim:

1. A new cultivar of hardy herbaceous perennial *Hibiscus* hybrid plant named 'Valentine's Crush' as herein illustrated and described.

* * * * *